United States Patent [19]
Lai et al.

[11] Patent Number: 5,766,144
[45] Date of Patent: Jun. 16, 1998

[54] HIGH EFFICIENCY ELECTRODE SYSTEM FOR IONTOPHORESIS

[75] Inventors: Ziping Lai, Oakland, Calif.; Keiichiro Okabe, Tokyo, Japan

[73] Assignee: Kabushiki Kaisya Advance, Tokyo, Japan

[21] Appl. No.: 566,470

[22] Filed: Dec. 4, 1995

[30] Foreign Application Priority Data

Dec. 5, 1994 [JP] Japan .................. 6-329241

[51] Int. Cl.$^6$ .................. A61N 1/30
[52] U.S. Cl. .................. 604/20
[58] Field of Search .................. 128/639; 604/20, 604/289; 607/115

[56] References Cited

U.S. PATENT DOCUMENTS

| | | |
|---|---|---|
| 4,287,032 | 9/1981 | Pellegri . |
| 4,722,726 | 2/1988 | Sanderson et al. . |
| 4,764,164 | 8/1988 | Sasaki . |
| 4,915,685 | 4/1990 | Petelenz et al. . |
| 4,927,408 | 5/1990 | Haak et al. .................. 604/20 |
| 5,084,008 | 1/1992 | Phipps .................. 604/20 |
| 5,284,571 | 2/1994 | Vebrugge . |
| 5,543,098 | 8/1996 | Meyers et al. .................. 604/20 |
| 5,558,633 | 9/1996 | Phipps et al. .................. 604/20 |

FOREIGN PATENT DOCUMENTS

| | | |
|---|---|---|
| 0 182 520 | 5/1986 | European Pat. Off. . |
| 0 542 284 A1 | 5/1993 | European Pat. Off. . |
| 0 556 112 A1 | 8/1993 | European Pat. Off. . |
| 2 463 200 | 7/1980 | France . |

*Primary Examiner*—Michael Powell Buiz
*Assistant Examiner*—Ellen S. Tao
*Attorney, Agent, or Firm*—Finnegan, Henderson, Farabow, Garrett & Dunner, L.L.P.

[57] ABSTRACT

An electrode system for administration of a pharmaceutical by iontophoresis which is comprised of an electroconductive substrate and a functional polymer having ammonium hydroxide or a quaternary ammonium halogen salt, sulfonic group, carboxylic group, amine group.

11 Claims, 4 Drawing Sheets

C$^+$: ION GENERATED FROM ELECTRODE DUE TO CURRENT
X$^-$: COUNTER ION OF POLYMER
D$^+$: PHARMACEUTICAL ION
Y$^-$: PHARMACEUTICAL COUNTER ION
CX: PRECIPITATE OR NONIONIC SUBSTANCE

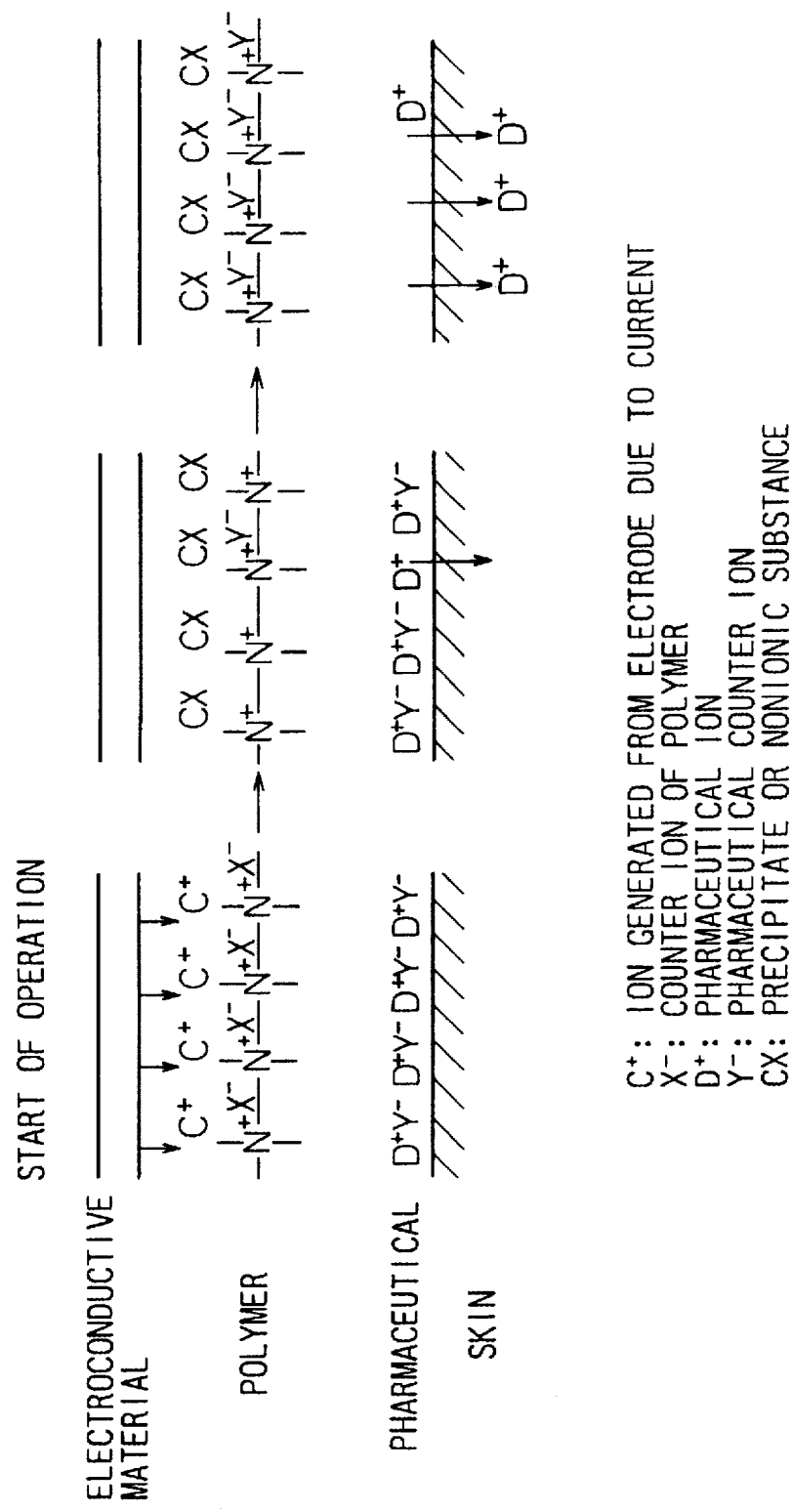

HIGH EFFICIENCY ELECTRODE SYSTEM FOR IONTOPHORESIS

BACKGROUND OF THE INVENTION

1. Field of the Invention

The present invention relates to a novel and highly efficient electrode system for iontophoresis as a system for transdermal administration of a pharmaceutical. This system combines a special electroconductive material and functional polymer so as to chemically trap ions generated on the surface of an applicator electrode at the time of operation, to act itself as a polymer electrode, to restrict the amount of coexisting competing ions generated into aqueous pharmaceutical solution in contact with the surface of skin of a subject, and to enhance the efficiency of electrical delivery of the desired pharmaceutical, that is, the delivery rate, and therefore, is expected to be highly useful in iontophoretic administration of pharmaceuticals or in cosmetics treatments.

2. Description of the Related Art

Iontophoresis is a technique for enhancing the transdermal permeation of ionized substances by a weak current. In recent years, advances in biotechnology have led to the successful development of numerous peptides or proteins useful as pharmaceuticals, such as, insulins, calcitonin, growth hormones, erythropoietin, etc. These peptide pharmaceuticals exhibit high efficacy in small amounts, but generally injection rather than oral administration is used for the application due to the problems of the activity of the proteinase in the gastrointestinal tract. In order to satisfy the desire to eliminate the problems associated with injections, that is, pain, troublesome, compliance, etc. and to cope with the fundamentals of pharmacology, the research and development of the iontophoretic transdermal drug delivery system became again active in the world. Iontophoresis devices are now available that are small in size, portable, and adhesively attachable. They are safe, free from the feeling of electricity even during operation, and have flexibility for many different drug delivery programs. A depolarized high-frequency pulse iontophoresis device is disclosed in, for example, Sasaki M. et al, U.S. Pat. No. 4,764,164.

Generally two electrodes are used in iontophoresis devices. That is, one electrode is a donor electrode which contains the ionized pharmaceutical and which causes the pharmaceutical to permeate into the body by application of a current. The other electrode is a counter electrode, which is separately placed on the skin from the other to form a circuit. When the pharmaceutical which is to be delivered has a positive charge (plus charge), the anodic electrode acts as a donor electrode and the cathode functions as a counter electrode to form a circuit. Conversely, when the pharmaceutical has a negative charge (minus charge), the cathode is a donor electrode and the anode becomes a counter electrode. In order to deliver a certain pharmaceutical by iontophoresis, a reservoir containing an ionized pharmaceutical is required. Various patents have been filed for applicators containing electrodes and reservoirs. In all cases, however, either there is a lack in efficiently eliminating the coexisting ions which are electrically generated from the electrode during iontophoresis and inevitably reduce the transport efficiency of the drug or else the construction of application is complicated.

During the iontophoresis operation, positively-charged ions are generated at the anodic side by the electrode oxidation reaction and negatively-charged ions are generated at the cathodic side by an electrode reduction reaction. The electrodes may be roughly divided into the following three types:

1) Inert electrodes (for example, carbon electrodes)
   Anode: $2H_2O \rightarrow 4H^+ + O_2 + 4e^-$
   Cathode: $2H_2O + 4e^- \rightarrow H_2 + 2OH^-$ 2) Active electrodes (Ag/AgCl electrodes etc.)

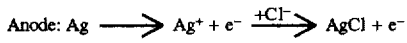

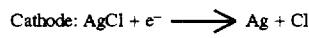

3) Organic oxidation reduction electrodes (quinone, aminal, etc.)

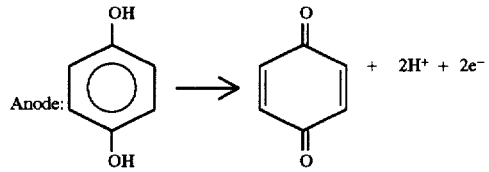

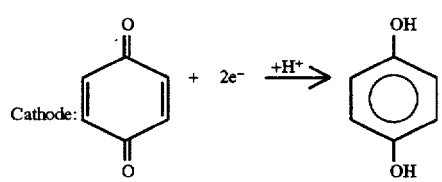

There is a quantitative relationship between the current applied and the ions generated. This is shown by the Faraday equation:

$$Q = F \times W / Me$$

where, Q: amount of current
F: Faraday constant
W: Weight
Me: Molecular equivalent During iontophoresis, the ions newly generated from the electrode compete with the drug ions electrically and the delivery rate of the drug (i.e., transport efficiency) is reduced inevitably. In order to solve this problem of the decrease in the drug delivery efficiency, three methods have been reported up to now.

The first method is to use an ion exchange membrane to separate the electrode space and the pharmaceutical space in the applicator structure, whereby the effects of the competing ions are eliminated (see Sanderson J. E., U.S. Pat. No. 4,722,726 (1988). The second method is to first exchange the pharmaceutical with an ion exchange resin and then exchanged with the hydrogen ion $H^+$ or $OH^-$ generated during the operation, whereby the pharmaceutical is released from the ion exchange resin and the competing ions are removed (see Petelenz T. J., U.S. Pat. No. 4,915,685 (1990)). The third method is to form a precipitate by a combination of a special metallic electrode and pharmaceutical or to cause neutralization, whereby the coexisting competing ions are removed (see Unterrecker, European Patent No. 0182520). These methods all make the construction of the applicator complicated, and raise the cost of manufacturing, and are unsuitable for practical use in many respects. Furthermore, in the third method combinations are limited for specific electrodes and pharmaceuticals (for example, iontophoresis of its peptides by acetates salt, etc.).

SUMMARY OF THE INVENTION

As explained above, to solve the problems and disadvantages in iontophoresis, the objects of the present invention are to eliminate the ions generated in the iontophoresis electrode applicator and to improve the efficiency of skin permeation of the drug and, further, to simplify the construction of the drug applicator.

In accordance with the present inventions, there is provided an electrode system for iontophoresis comprising a mixture of an electroconductive material and a functional polymer having a group of ammonium hydroxide or a quaternary ammonium halogen salt, sulfonic group, carboxylic group, amine group.

In accordance with the present invention, there is also provided an applicator for administering a pharmaceutical by iontophoresis using the above-mentioned electrode system.

BRIEF DESCRIPTION OF THE DRAWINGS

The present invention will be better understood from the description set forth below with reference to the accompanying drawings, in which:

FIG. 1 is a view for explaining the efficiency of the present invention;

DESCRIPTION OF THE PREFERRED EMBODIMENTS

Figure 2A:
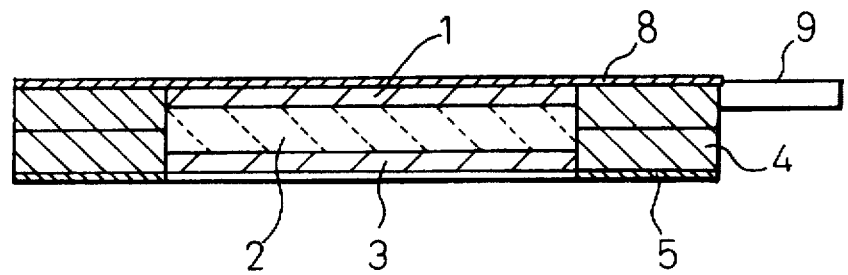
FIGS. 2(A), 2(B) and 2(C) are views showing an embodiment of the present invention.

In order to solve the above-mentioned problems, the present inventors have intensively studied to thereby complete the following invention. That is, as shown in FIG. 1, a composite of an electroconductive material and a polymer was structured so that the ionized charge generated at the surface of the electroconductive material due to the operation be allowed to transfer to the electroconductive polymer and provide a charge to the polymer, whereby the polymer per se functions as an electrode. That is, the competition is eliminated by immobilizing the charged ions competing with the pharmaceutical ions generated by electrolysis at the surface of the electrode. That is, the newly generated ions are eliminated by counter ions present in the polymer. Two approaches are used to achieve this object. One is to allow the ions to be precipitated, while the other is to allow to form a non-releasable covalent compound.

First Embodiment

In this the case the iontophoretic pharmaceutical-containing electrode (i.e., donor electrode) is an anodic active electrode and a silver (Ag) electrode is selected.

Efficiency can be increased by using a polymeric quaternary ammonium salt having a chlorine ion (Cl⁻) source on the surface of the silver electrode. That is, the silver ions ($Ag^+$) generated from the surface of the electrode due to the operation react with the chlorine ions ($Cl^-$) present in the polymer matrix and precipitate as AgCl and simultaneously the polymer takes on a positive charge. In this way, a difference in potential of the ion concentrations occurs and therefore a state close to one free of competing ions is approached. Therefore a high efficiency of delivery of the pharmaceutical can be obtained compared with the conventional iontophoresis electrode system.

Here, instead of the chlorine ions ($Cl^-$), a similar precipitate can be obtained by using iodine ions ($I^-$), bromine ions ($Br^-$), and other halogen ions and a similar effect of raising the delivery rate can be obtained.

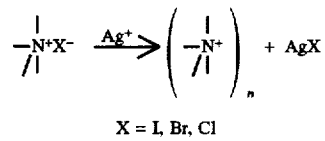

X = I, Br, Cl

Second Embodiment

In this case the iontophoretic pharmaceutical administering electrode (i.e., donor electrode) is an anodic inert electrode.

It is possible to improve the efficiency of iontophoretic delivery of the pharmaceutical by disposing a polymer having a hydroxy ion ($OH^-$) source around the surface of the inert electrode. Thus, it is possible to have the ions ($H^+$) generated by the operation react with the hydroxy ions ($OH^-$) in the polymer matrix whereby the coexisting competing ions can be removed and the rate of permeation of the pharmaceutical can be increased.

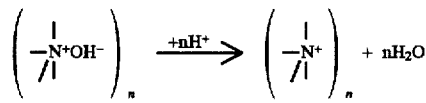

Third Embodiment

In this case the iontophoretic pharmaceutical administering electrode (i.e., donor electrode) is a cathode and where the active electrode is a silver chloride (AgCl) electrode.

Since a chlorine ion ($Cl^-$) is generated from the silver chloride electrode and becomes the ion competing with the negatively ionized pharmaceutical, for example, by coating a polymer (R—COOAg) having—COOAg group as a functional group, the released silver ion ($Ag^+$) reacts with the chlorine ion ($Cl^-$) released from the electrode, and therefore, the competing chlorine ion ($Cl^-$) can be removed and the rate of permeation of the ionic pharmaceutical (i.e., delivery rate) can be increased.

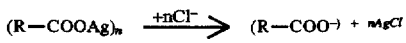

wherein R represents backbone of hydro carbon polymers.

Forth Embodiment

In this case the iontophoretic pharmaceutical administering electrode (i.e., donor electrode) is an inert electrode of carbon.

By using a polymer having simultaneously a tertiary amine and sulfonic group, the proton ($H^+$) or hydroxy ion ($OH^-$) generated at the surface of the electrode is trapped and the competing ion is removed. Therefore, the rate of permeation of the ionized pharmaceutical (i.e., rate of delivery) can be improved.

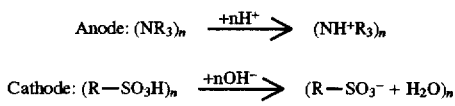

Anode: $(NR_3)_n \xrightarrow{+nH^+} (NH^+R_3)_n$

Cathode: $(R-SO_3H)_n \xrightarrow{+nOH^-} (R-SO_3^- + H_2O)_n$

EXAMPLES

The present invention will now be further illustrated by, but is by no means limited to, the following Examples, wherein all percentages are expressed on a weight basis unless otherwise noted.

Figure 2B:
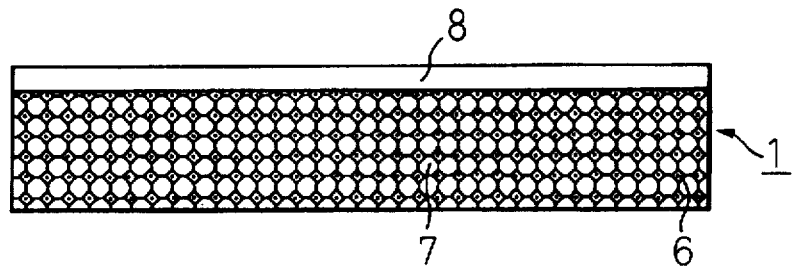
Figure 2C:
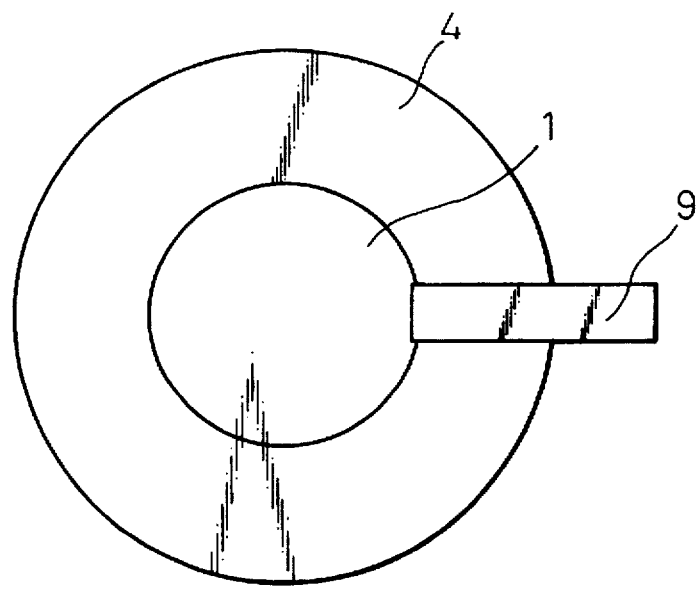

FIGS. 2(A), (B) and (C) are a view of an embodiment of the present invention, wherein FIG. 2(A) is a central sectional view, FIG. 2(B) is a schematic view of the electrode portion, and FIG. 2(C) is a top plan view.

In FIG. 2(A), (1) is an electrode portion. As shown in FIG. 2(B), this is a mixture of electroconductive granules (here, silver granules) (6) and polymer granules (7). (2) is a gel member, which is comprised of PVA, etc. (3) is a contact member for contact with the surface of the skin of the subject and is formed by a unwoven fabric etc. (4) is a tape, which is comprised of a non-electroconductive member. The tape (4) is disposed so as to support the electrode portion (1), gel member (2), and contact member (3) from the edges and, for example, is formed from MICROFORM tape (manufactured by 3M). (5) is an adhesive member, which is provided so as to adhesively affix the entire assembly on the surface of the skin of the subject and for example is made of BLENDERM adhesive (manufactured by 3M). (8) is a support member, which is comprised of a non-electroconductive substrate and supports the electrode portion (1) and tape (4). (9) is an electroconductive terminal which is connected with the electrode portion (1) and forms an input portion for electrically connecting the electrode portion (1) and the external iontophoretic electric output unit (not shown). Further, it is possible, without using the electroconductive terminal (9), to dispose the iontophoretic electric output unit inside and make it integral. The pharmaceutical to be administered may be disposed in one or both of the gel member (2) and contact member (3) or on the surface of the same, although this is not particularly limited.

Fabrication of Film Electrode

An 8.5 g amount of silver ink (DW250H-5 (manufactured by Toyobo)), 1.5 g of ion exchange resin having a group of quaternary ammonium salt and made into microgranules (1X-8 (DOWEX manufactured by Dow chemical Co.)), and 1.0 g of a diluent (YC-180 (manufactured by Toyobo)) were mixed well and spread to a constant thickness on a PET film (thickness of 0.1 mm) using a doctor blade to print it. Further, this was preheated to 65° C. for 30 minutes, then heated at 150° C. for 30 minutes to remove the solvent and to obtain a new film electrode of a thickness of 128 μm.

On the other hand, the conventional electrode was made in the same manner by mixing 4.27 g of silver ink (DW250H-5 (manufactured by Toyobo)), 0.12 g of salt microgranules (average diameter of granules of 100 μm), and 0.5 g of a diluent (YC-180 (manufactured by Toyobo)) and coating the result on a PET film.

The above electrodes were cut in accordance with the shape of the applicator and used for the evaluation of electrode system.

Evaluation of Efficacy in Vitro (Method of Testing Permeation Through Excised Skin of SD Rats)

The efficacy of the electrodes was evaluated in a test of permeation of TRH (thyrotropin-releasing hormone) through skin excised from rats. SD rats were anaesthetized with ether and dilapidated, the skin of the stomach portion was removed, and the fatty tissue of the skin was cleanly removed using tweezers to make the excised skin. This was allowed to stand in physiological saline at 4° C. for 15 hours, then was cut into pieces of 3×3 cm (9 cm²) size which were then affixed to side-by-side dispersion cells (manufactured by Advance). The donor chamber was filled with 0.1 percent TRH acetate solution (1 ml) rinsed by distilled water. The receiver chamber (3.5 ml) was filled with a 3-fold dilution of physiological saline, then was left for 60 minutes without operation, then subject to operation (electrical conditions: DC, 0.39 mA/cm²) for 60 minutes, then samples (0.2 ml) were taken from the receiver solution over time over a period of 120 minutes and the amount of TRH permeated through the film was measured by HPLC. After samples were taken, fresh 3-fold diluted physiological saline was supplemented. The measurement conditions of the HPLC were an HLPC apparatus of Model 6A (manufactured by Shimadzu Seisakusho), an immobilized phase of Inertsil ODS-2 4.6×150 mm, an eluent of 5 mM IPC-SDS aqueous solution: methanol=40:60 (pH=3.6, adjusted with phosphoric acid).

Figure 3:
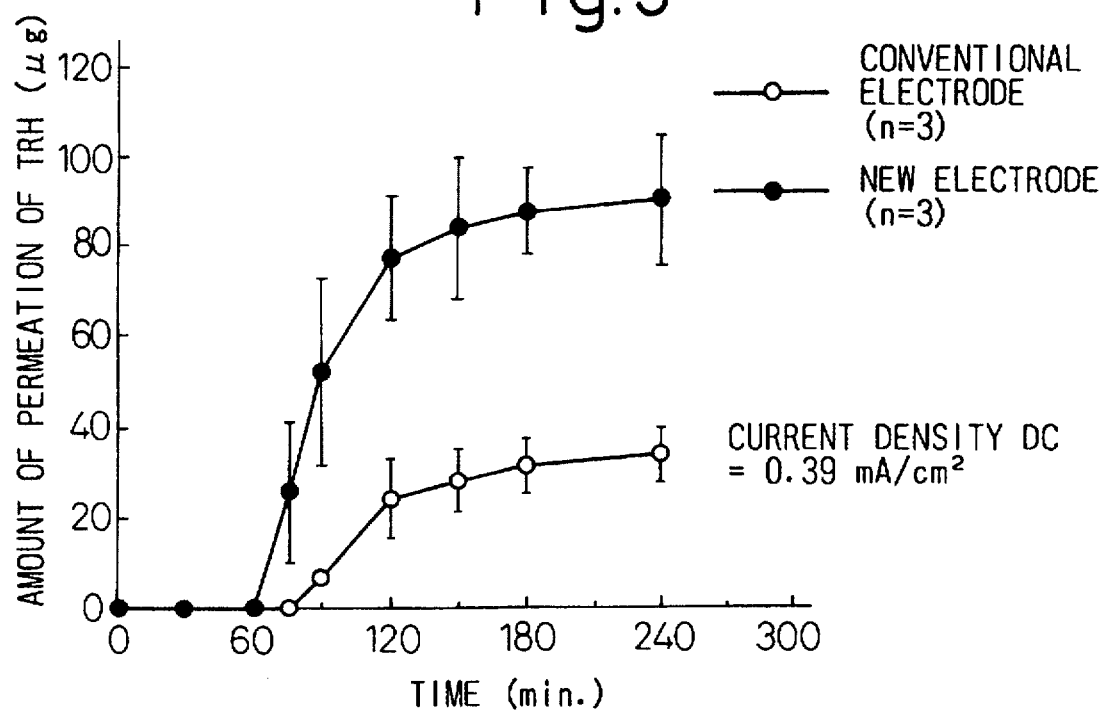
FIG. 3 is a graph for explaining the present invention under an applied DC in vitro.

FIG. 3 shows the relationship between the amount of permeation of the TRH acetate across exist skin under an applied direct current.

Result 1

As shown in FIG. 3, before iontophoretic operation, no permeation of TRH through the skin was observed. However, after one hour of operation (1 mA constant current, DC), the amount of permeation was 24±9 μg (mean value ±standard error) for the conventional electrode. For the new electrode, the amount of penetrated TRH was 77±13 μg (mean value ± standard error) an amount transported 3 times as much as that incorporated with conventional electrode.

Result 2

Figure 4:
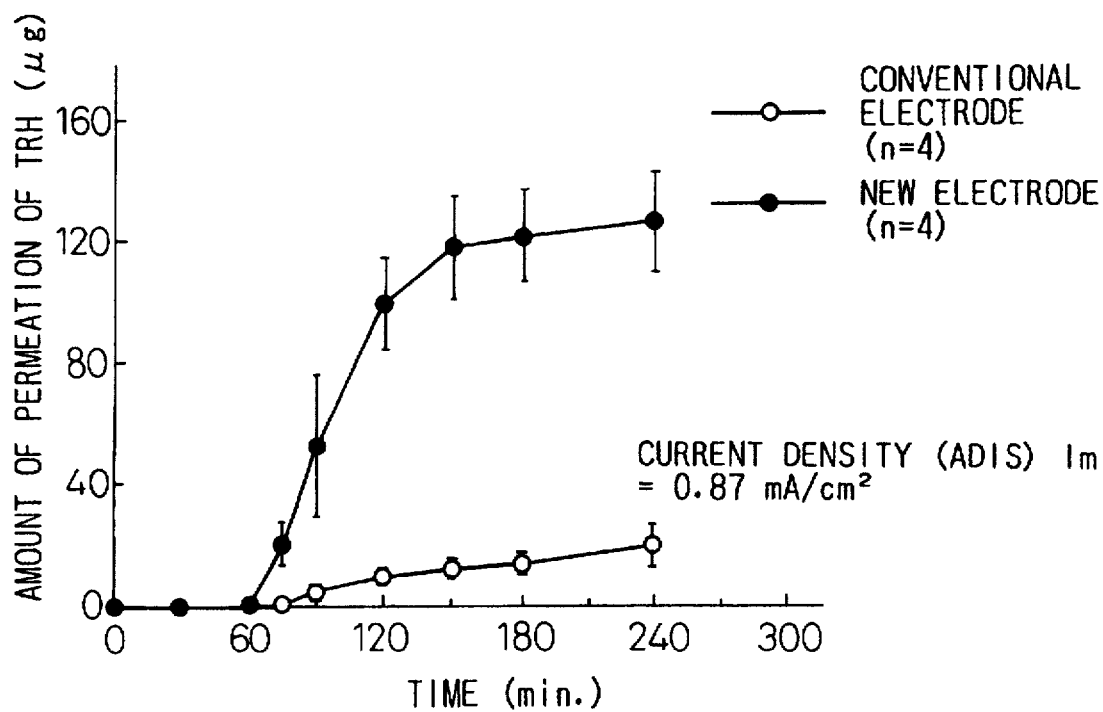
FIG. 4 is a graph explaining the efficiency of the present invention under a pulse depolarizing current (ADIS 4030) in vitro.

Further, as shown in FIG. 4, the new electrode exhibited an efficiency of drug delivering about six times greater than the conventional electrode (127±17 μg/20±7 μg (new/conventional), mean value ± standard error) even under conditions of operation (2 mA) with a depolarizing pulse iontophoresis system at the current density of 0.87 mA/cm² (ADIS; 40 kHz, 30% duty, made by Advance).

Evaluation of Efficacy of Electrode in Vivo (Method of Transdermal Drug Administration to SD Rats)

Method: SD rats were anaethetized by medicinal ether, their stomach portions were shorn by shears, and then were shaved by shavers. The stomach portions were cleaned with absorbent cotton containing 70% alcohol, then applicators having the new electrodes and/or applicators having the conventional electrodes were attached to the stomachs of the rats (n=3). For the counter electrode, a PVA physiological saline gel on AgCl electrode was used. The rats were placed in immobilizers (made by Natsume Seisakusho) and allowed to stand without current for one hour, then with current (ADIS, 40 kHz, 30% duty) for one hour. The blood sampling (0.5 ml) were carried out −60, 0, 30, 60, and 120 minutes, from tail vein of tail blood taken each time. The obtained blood samples were centrifuged (10,000 rpm/5 min) and the supernatents were used as the sample serums. The measurement of the TRH levels in the serums was entrusted to Mitsubishi Petrochemical BCL and was by RIA.

Result 3

Figure 5:
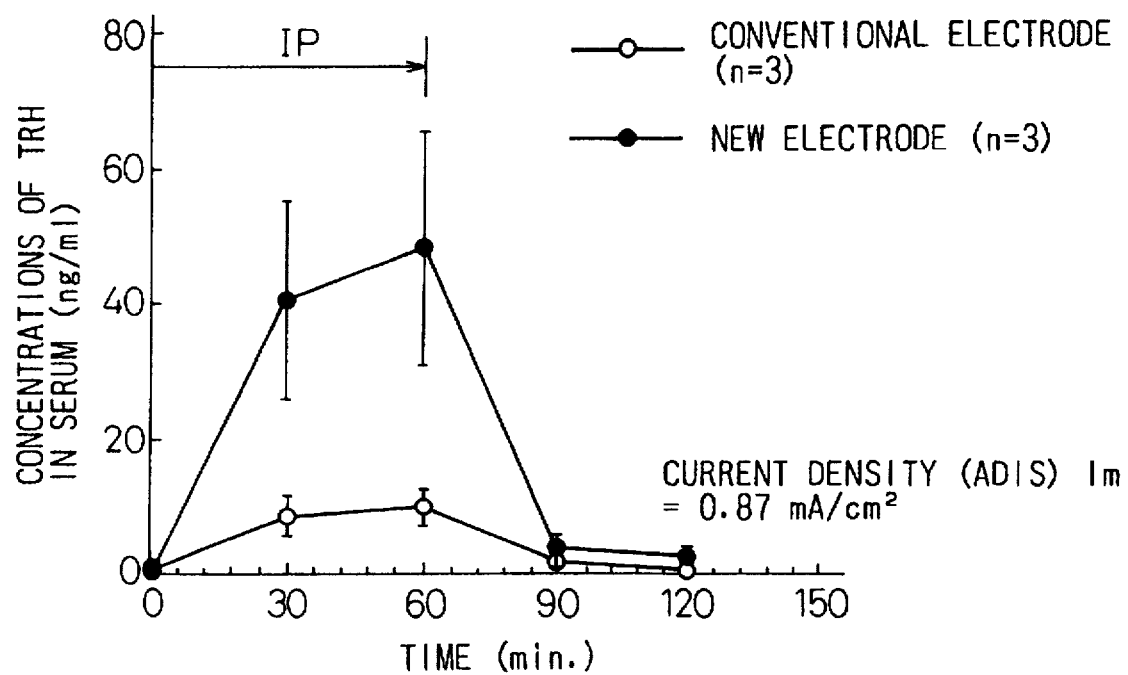
FIG. 5 is a graph for explaining the present invention using ADIS 4030 in vivo.

As shown in FIG. 5, after the start of iontophoresis, the plasma concentration of TRH increased. After 30 minutes, a steady level of 10±2.8 ng/ml was exhibited in the case of conventional electrodes, while the level was a high one of 40 ng/ml or more with the new electrodes, i.e., approximately four times the concentration in the blood was achieved.

The typical embodiments of the present invention can be embodied as follows.

1. An electrode system for iontophoresis comprising an electroconductive material or substrate and a functional polymer having at least one member selected from the group consisting of ammonium hydroxide, a quaternary ammonium halogen salt, sulfonic group, carboxylic group, amine group, or other functional groups.

2. An electrode system for iontophoresis as set forth in item 1, wherein said electroconductive material is safe to the body and for example comprises granules or foil of one or more of silver, iron, gold, platinum, titanium, and other metal materials and carbon, graphic, and other non-metallic materials.

3. An electrode system for iontophoresis as set forth in item 1, wherein said quaternary ammonium halogen salt is, for example, a chloride or a bromide or an iodide etc.

4. An electrode system for iontophoresis as set forth in item 1, wherein said functional polymer is a mixture of one or more of a carboxymethyl cellulose system, acrylate system, vinyl alcohol system, vinyl pyrrolidone system, styrene system, and etc.

5. A film electrode system wherein the electrode system set forth in item 1 is made by mixing an ink containing an electroconductive material (for example, silver) and a polymer having quaternary ammonium chloride and printing this on a film.

6. An anode electrode system wherein the electrode system of item 1 is, for example, comprised of a combination of the following, that is, an iron electroconductive material and a polymer having ammonium hydroxide.

7. A cathode electrode system wherein the electrode system of item 1 is for example comprised of a combination of the following, that is, a silver chloride/silver (AgCl/Ag) electroconductive material and a polymer having a carboxy-silver salt group (—COOAg).

8. An anode or cathode electrode system wherein the electrode system of item 1 is, for example, comprised of a combination of the following, that is, an inert electroconductive material and a polymer having an amine group and sulfonic group or carboxylic group.

9. An anode or cathode electrode system wherein the electrode system of item 1 is, for example, comprised of a combination of the following, that is, an inert electroconductive material and a polymer having a quinone or aminal functional group and amine group and sulfonic group or carboxylic group.

10. An applicator for administering a pharmaceutical by iontophoresis using the electrode system set forth in item 1.

11. An applicator for administering a pharmaceutical by iontophoresis as set forth in claim 10, which has a simple and safe patch structure comprised of just the electrode of item 3 and a pharmaceutical reservoir.

12. An applicator for administering a pharmaceutical by iontophoresis as set forth in claim 10, wherein the reservoir of item 11 is a gel including a pharmaceutical and a cellulose or nylon porous substrate.

As explained above, according to the present invention, there is provided an electrode system for administration of a pharmaceutical by iontophoresis, wherein the ions generated from the surface of the electroconductive material of the electrode portion are immediately made insoluble and captured by the functional polymer surrounding the substrate whereby the ions competing with the pharmaceutical ions can be removed from the electric field. Therefore, the delivery rate in the transdermal permeation of the pharmaceutical is improved and, as a result, an effect of the efficiency of pharmaceutical utilization is improved. Furthermore, the completed electrode system itself is simple in the construction, and therefore, it is possible to fabricate an iontophoretic device into a small patch easy to use. And its manufacturing cost can be reduced.

We claim:

1. In an applicator for administering a pharmaceutical by iontophoresis including an electrode portion, the improvement comprising (A) a composite electrode as the electrode portion comprising a mixture of (i) an electroconductive material and (ii) a functional polymer, said composite electrode being in the form of a film and being made by mixing an ink containing the electroconductive material and a polymer having a quaternary ammonium halogen salt to form a mixture and printing this mixture on a film and (B) a separate reservoir for holding a pharmaceutical adjacent to said composite electrode.

2. The applicator of claim 1, wherein said electroconductive material is safe to the body and comprises at least one member selected from the group consisting of silver, iron, gold, platinum, titanium, carbon, and graphite.

3. The applicator of claim 1, wherein said quaternary ammonium halogen salt is a chloride, a bromide, or an iodide.

4. The applicator of claim 1, wherein said functional polymer is at least one member selected from the group consisting of a carboxymethyl cellulose, an acrylate, a vinyl alcohol, a vinyl pyrrolidone, and a styrene.

5. The applicator of claim 1, wherein the reservoir is a gel including a pharmaceutical and a cellulose or nylon porous substrate.

6. In an applicator for administering a pharmaceutical by iontophoresis including an electrode portion, the improvement comprising (A) a composite electrode as the electrode portion comprising a mixture of (i) an electroconductive material and (ii) a functional polymer, said composite electrode being in the form of an anode electrode and comprised of a mixture of an iron electroconductive material and a polymer having ammonium hydroxide and (B) a separate reservoir for holding a pharmaceutical adjacent to said composite electrode.

7. The applicator of claim 6, wherein said functional polymer is at least one member selected from the group consisting of a carboxymethyl cellulose, an acrylate, a vinyl alcohol, a vinyl pyrrolidone, and a styrene.

8. The application of claim 6, wherein the reservoir is a gel including a pharmaceutical and a cellulose or nylon porous substrate.

9. In an applicator for administering a pharmaceutical by iontophoresis including an electrode portion, the improvement comprising (A) a composite electrode as the electrode portion comprising a mixture of (i) an electroconductive material and (ii) a functional polymer, said composite electrode being a cathode electrode and comprised of a mixture of a silver chloride/silver electroconductive material and a polymer having a carboxy-silver salt group and (B) a separate reservoir for holding a pharmaceutical adjacent to said composite electrode.

10. The applicator of claim 9, wherein said functional polymer is at least one member selected from the group consisting of a carboxymethyl cellulose, an acrylate, a vinyl alcohol, a vinyl pyrrolidone, and a styrene.

11. The applicator of claim 9, wherein the reservoir is a gel including a pharmaceutical and a cellulose or nylon porous substrate.

* * * * *